United States Patent [19]

Itil et al.

[11] 3,954,988

[45] May 4, 1976

[54] USE OF LISURIDE AND PHYSIOLOGICALLY ACCEPTABLE SALTS THEREOF TO ACHIEVE PSYCHIC ENERGIZER EFFECTS

[75] Inventors: Turan M. Itil, Nyack, N.Y.; Werner Martin Herrmann, Berlin, Germany

[73] Assignee: Schering Aktiengesellschaft, Berlin & Bergkamen, Germany

[22] Filed: Nov. 22, 1974

[21] Appl. No.: 526,303

[30] Foreign Application Priority Data

Nov. 24, 1973 Germany............................ 2359128

[52] U.S. Cl. ................................................ 424/261
[51] Int. Cl.² ............................................. A61K 31/48
[58] Field of Search ..................................... 424/261

[56] References Cited
UNITED STATES PATENTS 3,681,497   8/1972   Semonsky et al................... 424/261

Primary Examiner—Stanley J. Friedman
Attorney, Agent, or Firm—Millen, Raptes & White

[57] ABSTRACT

Lisuride and its acid addition salts are used to achieve psychic energizer effects.

7 Claims, No Drawings

USE OF LISURIDE AND PHYSIOLOGICALLY ACCEPTABLE SALTS THEREOF TO ACHIEVE PSYCHIC ENERGIZER EFFECTS

BACKGROUND OF THE INVENTION

This invention relates to lisuride and the physiologically acceptable salts thereof and their use.

It is known from Canadian Pat. No. 885,976 that lisuride hydrogen maleate is suitable as a serotonin antagonist for the treatment of migraine, allergies, the dumping syndrome, and argentaffinoma. Heretofore, nothing has been reported regarding any psychotropic effect of lisuride hydrogen maleate.

For the most part, phenylethylamine derivatives, such as amphetamine and methamphetamine have been used as psychopharmacological agents with a psychic energizer effect.

These effective agents have a high toxicity. Furthermore, they have the disadvantage that they exert a stimulating effect and a phase of exhaustion occurs after their use. It has been reported that these substances evoke psychotic conditions and that these symptoms are very similar to the clinical picture of paronoic schizophrenia. Also, a tolerance with respect to the effectiveness of the compounds develops. Additionally, the amphetamines exhibit great dependency and abuse potential.

SUMMARY OF THE INVENTION

According to this invention, psychic energizer effects are achieved by the administration of lisuride or a physiologically acceptable acid addition salt thereof in daily dosages effective to ameliorate a pyschic disturbance.

Physiologically acceptable salts of lisuride are the acid addition salts with inorganic and organic acids. Especially suitable for the salt formation are, for example, hydrochloric acid, methanesulfonic acid, glucoheptanoic acid, succinic acid, tartaric acid, maleic acid, etc. A preferred salt is lisuride hydrogen maleate.

Lisuride [N-(D-6-methyl-8-isoergolenyl)-N',N'-diethylurea] hydrogen maleate is described, for example, in Belgian Pat. No. 703,487. Other physiologically acceptable salts thereof can be prepared analogously. In the examples hereinafter, a molar equivalent of another acid can be substituted for the hydrogen maleate acid addition salt.

It has been found that lisuride and the physiologically compatible salts thereof are psychic energizers without simultaneously exhibiting the disadvantages (stimulating activity and dependency creation) of the phenylethylamine derivatives. There is a significant therapeutic effect in so-called neurasthenic symptomatology, mainly in the following symptoms loss of interest, loss of drive and activity, loss of energy and functional capacity, loss of concentration and learning ability. Even after long-term use of lisuride hydrogen maleate, there is no indication of the development of a dependency.

The spectrum of psychic energizer effectiveness, discovered with the aid of the quantitative Pharmaco-EEG is completely novel and has not been found heretofore for another medicinal agent. The objective results are laid down in parameters of the EEG's analyzed by computers and the spectrum of effectiveness is characterized by a lowering of the delta and theta waves, an increase in the alpha and slow beta waves, as well as a lowering of the fast beta waves and the fast waves up to 100/sec. These phenomena affecting the physiology of the brain point to certain stimulating and simultaneously inhibiting effects exerted by lisuride. Accordingly, lisuride has a clinical picture of activity which can be called "energizer".

Lisuride and the physiologically compatible salts thereof have been tested in man in a placebo-controlled double blind experiment by quantitative Pharmaco-electroencephalography (CEEG) (T. M. Itil et al., "Nervenarzt" [Neurologist] 44 [1973] 65). The effects and side effects were determined by various rating scales, for example for neurological and psychosomatic symptomatology, by self-rating scales for sedation, anxiety and depression, as well as by means of physicians' interviews.

Upon administration of lisuride and the physiologically compatible salts thereof, the desired effect occurs shortly after administration, viz., after about 2–3 hours. This is surprising, since in the prophylactic treatment of migraine with lisuride hydrogen maleate the therapeutic effect can be achieved only after 3–4 weeks of therapy.

The invention also relates to a method for the treatment of patients of any age suffering from disturbances of drive and interest, and disturbances of mood, behavior, energy, and functional capacity, with the medicinal agents of this invention. Among these disturbances are phenomena such as adynamiz, apathy, lack of energy, lack of drive, drop in efficiency, loss of interest, disturbances of the powers of concentration and memory. This can refer, for example, to psychophysiological disturbances, the so-called "tired housewife syndrome," to children and juveniles with thinking, concentration or behavorial disturbances or learning problems, or to patients of any age, but especially older patients having problems such as weakness of memory and concentration and a general drop in efficiency. The effect also relates to children having hyperkinetic conditions, and/or behavioral disturbances and to geriartric patients with the same symptomatology as given for adolescens and adults but also with severe disturbances in mental function like chronic brain syndrome.

In medical practice, the medicinal agents of this invention, based on lisuride and the physiologically acceptable acid addition salts thereof, can be administered subcutaneously, intramuscularly, but preferably per os.

The daily dosage is 1–300 µg., preferably 1–40 µg. The whole dose can be administered all at once or in several divided doses. The agents of this invention are also suitable for a long-term treatment, since no psychic dependency is produced.

The special drug preparations are produced in a conventional manner by processing the lisuride or a physiologically acceptable salt thereof with the vehicles, diluents, flavor-ameliorating agents, etc., customary in galenic pharmacy.

Suitable for injections are especially oily solutions or suspensions, e.g., solutions or suspensions in sesame, castor and cottonseed oil.

To prepare intramuscular depot forms, the effective agents can be suspended or dissolved in fatty oils according to conventional methods. Such depot forms contain about 10–500 µg. of effective agent per unit of application; the effective agent is released over a time period of about 2 to 20 days.

The amount of active agent per parenteral unit of administration otherwise is about 2 – 600 µg., preferably 2 – 80 μg, per week.

The medicinal agents of this invention are suitable for oral application particularly in the form of tablets, capsules, dragees, pills, suspensions and solutions.

The amount of active agent per oral unit of administration is 1 – 100 μg., preferably 1–20 μg.

Also suitable are oral timed-release forms obtained in the usual manner, for example, by adding hydrogenated fats and processing with resin-forming agents.

Drops for oral administration can be produced by suspending the effective agent in oils with the addition of flavor-ameliorating agents and/or solubilizers, for example, 5 – 40 μg. of the active agent in a daily dosage of 3 × 10 drops.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

| | |
|---|---|
| 0.025 mg. | Lisuride hydrogen maleate (micronized) |
| 0.200 mg. | Tartaric acid |
| 0.050 mg. | Disodium edetate |
| 59.325 mg. | Lactose |
| 20.000 mg. | Microcellulose |
| 0.400 mg. | Magnesium stearate |
| 80.000 mg. | | are mixed together homogeneously adn compressed, without previous granulation, into tablets with a breaking notch, having a weight of 80 mg.

EXAMPLE 2

| | |
|---|---|
| 0.005 mg. | Lisuride hydrogen maleate |
| 0.200 mg. | Tartaric acid |
| 0.050 mg. | Disodium edetate |
| 59.345 mg. | Lactose |
| 20.000 mg. | Microcellulose |
| 0.400 mg. | Magnesium stearate |
| 80.000 mg. | | are combined and compressed into tablets having a final weight of 80 mg. analogously to Example 1.

EXAMPLE 3

| | |
|---|---|
| 0.001 mg. | Lisuride hydrogen maleate |
| 0.200 mg. | Tartaric acid |
| 0.050 mg. | Disodium edetate |
| 59.349 mg. | Lactose |
| 20.000 mg. | Microcellulose |
| 0.400 mg. | Magnesium stearate |
| 80.000 mg. | | are combined and compressed, analogously to Example 1, into tablets having a final weight of 80 mg.

EXAMPLE 4

Respectively 0.005 mg. of lisuride hydrogen maleate (micronized, particle size approximately 20 μm.) is mixed homogeneously with 150 mg. of lactose and filled into hard gelatin capsules (5 × 15 mm.).

A. Effects of Lisuride on Patients with "Geriatric" Syndrome

In an open pilot trial without any control drugs, the effects of lisuride has been studied in a group of six patients with an age range of 38–66. Lisuride in the form of its addition salt hydrogen maleate was given in daily dosages of 25 – 75 μg. for a period of 3 months.

Results of this study indicated:

In at least 3 patients in whom the symptoms of apathy and lack of drive and energy were predominant, lisuride was effective as "psychoenergizer". In two patients in whom the symptoms of organic brain syndrome were predominant, lisuride was effective, particularly at the beginning of treatment in the improvement of bladder and bowel control.

B. Effects of Lisuride on Behaviorally-Disturbed Children

Because of the psychostimulant-like CNS effects of lisuride, a group of seven behaviorally-disturbed and/or hyperkinetic children has been treated with lisuride in an open uncontrolled pilot trial. The children were diagnosed as hyperkinetic childhood behavior disorder with an age range of 3–18 years. They were treated with daily dosages of 12.5–50 μg. of lisuride hydrogen maleate for a period of 7–28 days.

Results of this study indicated: Four patients did show response, they became calmer and quieter. The hyperactivity and hyperkinetic movements were reduced. Three subjects did not show a significant improvement.

C. Effects of Lisuride on Neurasthenic States (Psychophysiological Disorders)

In a double-blind study with placebo control, the effects of lisuride have been investigated in a group of 21 patients who have been diagnosed as "neurasthenic" psychophysilogical disorder. 17 received placebo and 11 lisuride hydrogen maleate (LHM) in a daily dosage range of 5–50 μg. The patients were in an age range of 18–64 years and the duration of treatment was outlined for four weeks. The main symptomatology was loss of energy, drive, desire, and the ability to enjoy life, as well as a loss of memory and concentration. Five patients were dropped from the programme for various reasons before the first week of evaluation was completed.

The results of this study indicated that there is an effect on drive, energy, the ability to enjoy, as well as concentration and memory with LHM within four weeks of treatment.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for the treatment of psychic disturbances manifested by
   a. behaviorally disturbed and/or hyperkinetic children suffering from loss of concentration and memory and learning difficulties,
   b. adolescents and adults with so-called neurasthenic symptomatology with at least of the following symptoms: loss of interest, loss of drive and activity, loss of energy and functional capacity, loss of concentration and learning ability and c. geriatric patients with loss of interest, loss of drive and activity, loss of energy and functional capacity, loss of concentration and learing ability combined with severe disturbance in mental function, which comprises administering to the affected patient a dosage of N-D-6-methyl-8-isoergolenyl-N',N'-diethylurea or a physiologically acceptable acid addition salt thereof effective to ameliorate the psychic disturbance.

2. A method according to claim 1 wherein the administration is an oral daily dosage of 1 – 200 µg.

3. A method according to claim 2 wherein N-(D-6-methyl-8-isoergolenyl)-N',N'-diethylurea hydrogen maleate is administered orally in a dosage of 1 – 40 µg per day.

4. A method according to claim 1 wherein the administration is parenteral in a depot form.

5. A method according to claim 4 wherein the adminitration is subcutaneous or intramuscular.

6. A method according to claim 5 wherein N-(D6-methyl-8-isoergolenyl)-N',N'-diethylurea hydrogen maleate in depot form is administered in a dosage of 2 – 600 µg per week.

7. A method according to claim 6 wherein N-(D-6-methyl-8-isoergolenyl)-N',N'-diethylurea hydrogen maleate in depot form is administered in a dosage of 2 – 80 µg per week.

* * * * *